US00PP12676P2

(12) United States Plant Patent
Heuger

(10) Patent No.: US PP12,676 P2
(45) Date of Patent: Jun. 4, 2002

(54) BEGONIA PLANT NAMED 'PEGGY'

(76) Inventor: Josef Heuger, Munsterstrasse 49, 49129 Glandorf (DE)

( * ) Notice: Subject to any disclaimer, the term of this patent is extended or adjusted under 35 U.S.C. 154(b) by 0 days.

(21) Appl. No.: 09/641,717

(22) Filed: Aug. 21, 2000

(51) Int. Cl.[7] ..... A01H 5/00

(52) U.S. Cl. ..... Plt./344

(58) Field of Search ..... Plt./344, 343

(56) References Cited

PUBLICATIONS

UPOV–ROM GTITM Computer Database 2001/04, GTI Jouve Retrieval Software, citation for 'Peggy'.*

* cited by examiner

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Begonia plant named 'Peggy', characterized by its compact and freely branching plant habit; double dark pink and light yellow bi-colored flowers that are held above the foliage; and excellent postproduction longevity.

2 Drawing Sheets

BACKGROUND OF THE INVENTION

The present Invention relates to a new and distinct cultivar of Begonia plant, botanically known as *Begonia×hiemalis*, commercially known as Elatior Begonia, and hereinafter referred to by the name 'Peggy'.

The new Begonia was discovered by the Inventor in a controlled environment in Glandorf, Germany, January, 1999, as a naturally-occurring whole plant mutation of *Begonia×hiemalis* 'Carneval', U.S. Plant patent applications Ser. No. 09/641,719. The new Begonia was observed as a single plant in a group of flowering plants of the parent cultivar. The selection of this plant was based on its unique flower coloration and position of the flowers above the foliage.

Asexual reproduction of the new Begonia by leaf and terminal cuttings taken in a controlled environment in Glandorf, Germany, has shown that the unique features of this new Begonia are stable and reproduced true to type in successive generations.

SUMMARY OF THE INVENTION

The cultivar 'Peggy' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Peggy'. These characteristics in combination distinguish 'Peggy' as a new and distinct Begonia:

1. Compact and freely branching plant habit.
2. Double dark pink and light yellow bi-colored flowers that are held above the foliage.
3. Excellent postproduction longevity.

In side-by-side comparisons conducted by the Inventor in Glandorf, Germany, plants of the new Begonia differ from plants of the parent cultivar Carneval primarily in flower color. Plants of the new Begonia have dark pink and light yellow bi-colored petals whereas plants of the cultivar Carneval have red and yellow bi-colored petals. In addition, flowers of plants of the new Begonia are positioned above the foliage whereas flowers of plants of the cultivar Carneval are positioned at the foliage level.

BRIEF DESCRIPTION OF THE PHOTOGRAPHS

The accompanying colored photographs illustrate the overall appearance of the new Begonia, showing the colors as true as it is reasonably possible to obtain in colored reproductions of this type. Colors in the photographs may differ slightly from the color values cited in the detailed botanical description which more accurately describe the actual colors of the new Begonia.

The photograph on the first sheet comprises a top perspective view of a typical flowering plant of 'Peggy'.

The photograph at the top of the second sheet is a close-up view of the upper surfaces of typical developing flowers; and the photograph at the bottom of the second sheet is a close-up view of the lower surfaces of typical developing flowers of 'Peggy'.

DETAILED BOTANICAL DESCRIPTION

In the following description, color references are made to The Royal Horticultural Society Colour Chart except where general terms of ordinary dictionary significance are used. The following observations and measurements describe plants grown in Glandorf, Germany, under commercial practice in a glass-covered greenhouse. Average day and night temperatures were 20° C. during the first three to four weeks then lowered to an average day and night temperature of 19° C. until flowering. Four weeks after planting in 13-cm containers, one week of long nyctoperiods were given followed by short nyctoperiods of eight hours. Measurements and numerical values represent averages for typical flowering plants.

Botanical classification: *Begonia×hiemalis* cultivar Peggy.

Commercial classification: Elatior Begonia.

Parentage: Naturally-occurring whole plant mutation of *Begonia×hiemalis* cultivar Carneval, U.S. Plant Patent application filed concurrently with this application.

Propagation:

*Type.*—Terminal cuttings.

*Time to develop roots.*—About 28 days with soil temperatures of 20° C.

*Root description.*—Fine, fibrous and well-branched; plants typically do not form tubers.

Plant description:

*Plant form.*—Compact; upright potted plant, inverted triangle; freely branching with good stem and stem base strength. Flowers are double and abundant. Plants flower continuously.

*Growth habit.*—Moderate growth rate, vigorous. Suitable for 11 to 15-cm containers. Under optimal environmental and cultural conditions, usually about 4 months are required to produce proportional 13-cm potted plants from terminal cuttings. Vegetative shoots are formed at basal nodes and flowering shoots are formed at upper nodes.

*Plant height.*—About 23.5 cm.

*Plant width.*—About 28 cm.

*Leaves.*—Arrangement: Simple, alternate. Length: About 16.5 cm. Width: About 13 cm. Shape: Asymmetrical, more or less reniform. Apex: Acuminate. Base: Cordate. Margin: Doubly serrate. Texture: Glabrous. Petiole length: About 4.25 cm. Color, young and fully expanded leaves: Upper surface: 147A. Lower surface: 147C overlain with 184B. Venation, upper and lower surfaces: 148B. Petiole: 180C.

Flower description:

*Flower habit.*—Double flowers with numerous tepals arranged in axillary cymes. Usually 8 to 10 flowers per cyme. Many cymes in flower simultaneously. Flowers positioned above the foliage. Flowering continuous.

*Natural flowering season.*—Plants will flower year around regardless of nyctoperiod, however plants flower earlier and more abundantly from mid-February until November in the Northern Hemisphere.

*Flowers.*—Shape: Rounded. Diameter: About 5.25 cm. Depth (height): About 2 cm.

*Flower buds.*—Length: About 1.3 cm. Diameter: About 1.1 cm. Color: 145C.

*Tepals.*—Arrangement: Rosette. Shape: Rounded flabellate, broad; apex, rounded. Margin: Entire. Quantity per flower: Usually about 20 per flower. Size: Outer tepals: Length: About 2.9 cm. Width: About 3.4 cm. Inner tepals: Length: About 1.4 cm. Width: About 1.8 cm. Texture: Smooth, satiny, glabrous. Color: When opening: Apex to about mid-section of tepal, 50A; base to about mid-section of tepal, 4D; colors bleed together. Fully opened, upper surface: Apex to about mid-section of tepal, 50A; base to about mid-section of tepal, 4D; colors bleed together. Fully opened, lower surface: Apex to about mid-section of tepal, 50B; base to about mid-section of tepal, 4D; colors bleed together.

*Flower bracts.*—Arrangement: Two, opposite. Shape: Cordate; apex, apiculate. Margin: Serrate. Color, both surfaces: 144B.

*Peduncles.*—Angle: Erect. Length: About 4 cm. Texture: Glabrous. Color: 147C with slight anthocyanin blush.

*Pedicels.*—Angle: Bent. Length: About 2 cm. Texture: Glabrous. Color: 148C.

*Reproductive organs.*—Stamens: None observed. Pistils: None observed.

*Seed.*—Seed production has not been observed as reproductive organs are not formed.

Postproduction longevity:

*Individual flowers.*—Generally about 2 to 3 weeks.

*Whole plants.*—About 6 weeks under interior conditions.

Disease resistance: Resistance to diseases common to Begonia has not been observed.

It is claimed:

1. A new and distinct cultivar of Begonia plant named 'Peggy', as illustrated and described.

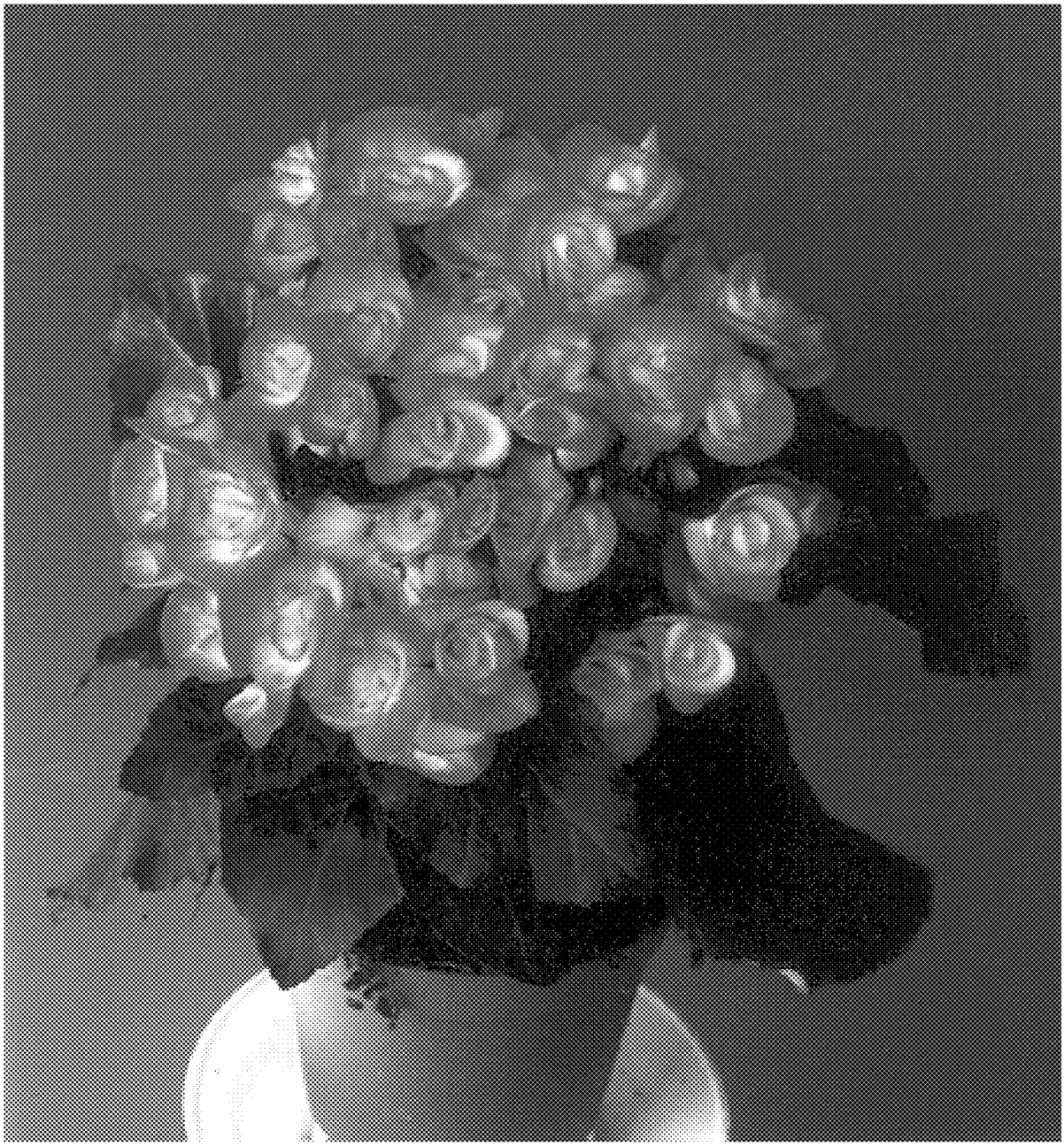

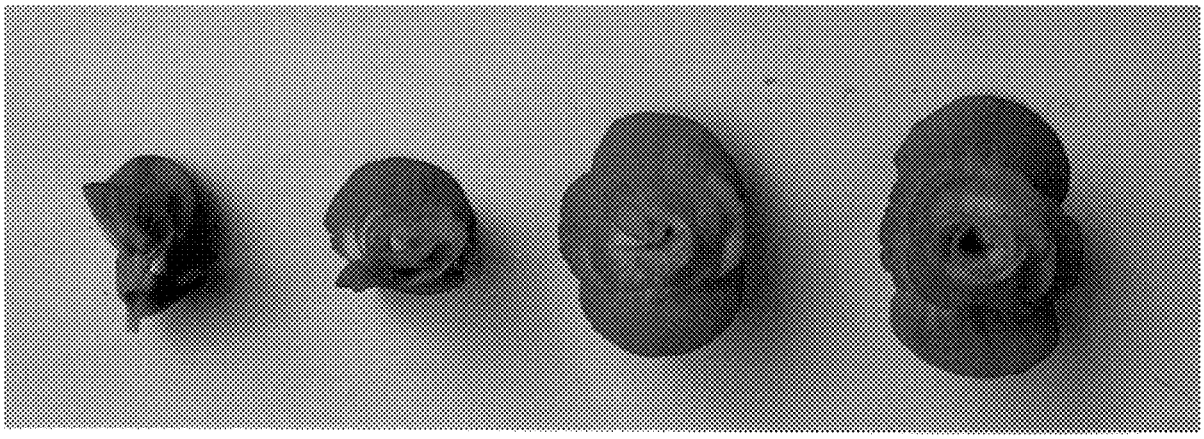
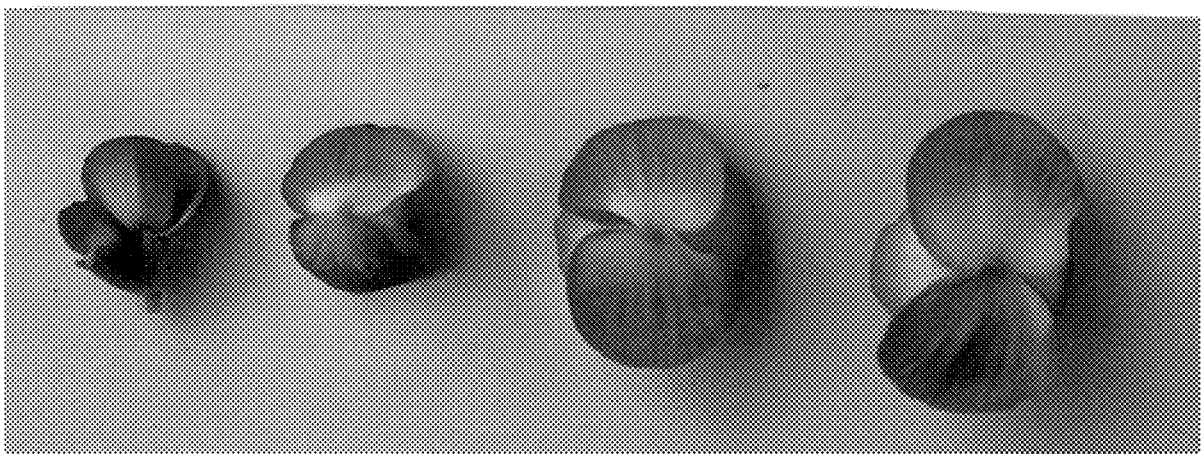

* * * * *